United States Patent
Yamamoto et al.

(10) Patent No.: US 10,517,485 B2
(45) Date of Patent: Dec. 31, 2019

(54) ACOUSTIC WAVE RECEIVING APPARATUS AND CONTROL METHOD THEREOF

(71) Applicant: CANON KABUSHIKI KAISHA, Tokyo (JP)

(72) Inventors: Takeshi Yamamoto, Tokyo (JP); Mitsuo Nishimura, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 9 days.

(21) Appl. No.: 15/607,840

(22) Filed: May 30, 2017

(65) Prior Publication Data

US 2017/0347889 A1 Dec. 7, 2017

(30) Foreign Application Priority Data

Jun. 6, 2016 (JP) ................................ 2016-112397

(51) Int. Cl.

| | |
|---|---|
| *A61B 8/08* | (2006.01) |
| *A61B 5/00* | (2006.01) |
| *G01S 15/89* | (2006.01) |
| *G01S 7/52* | (2006.01) |
| *A61B 8/00* | (2006.01) |

(52) U.S. Cl.

CPC .......... *A61B 5/0095* (2013.01); *A61B 5/4312* (2013.01); *G01S 7/52079* (2013.01); *G01S 15/8929* (2013.01); *G01S 15/8965* (2013.01); *A61B 5/742* (2013.01); *A61B 8/0825* (2013.01); *A61B 8/4209* (2013.01); *A61B 8/4483* (2013.01)

(58) Field of Classification Search

CPC .................................. A61B 5/0095; A61B 8/06
See application file for complete search history.

(56) References Cited

U.S. PATENT DOCUMENTS

| | | | |
|---|---|---|---|
| 2011/0306865 A1 | 12/2011 | Thornton et al. | |
| 2013/0237800 A1 | 9/2013 | Yamamoto | .................... 600/407 |
| 2016/0066793 A1 | 3/2016 | Yamamoto et al. | ......................... A61B 5/0095 |
| 2017/0035361 A1 | 2/2017 | Yamamoto | ........... A61B 5/0095 |
| 2017/0067994 A1* | 3/2017 | Tanaka | ................. A61B 8/4483 |
| 2017/0325692 A1* | 11/2017 | Nishihara | ............ A61B 8/0825 |
| 2017/0367656 A1* | 12/2017 | Ohishi | ................. A61B 5/0095 |

FOREIGN PATENT DOCUMENTS

JP 2015-205041 11/2015

* cited by examiner

*Primary Examiner* — Jewel V Dowtin

(74) *Attorney, Agent, or Firm* — Venable LLP

(57) ABSTRACT

An acoustic wave receiving apparatus is used, which includes: a holding member; a reception transducer array; a liquid vessel to which the reception transducer array is fixed and configured to store an acoustic matching liquid; a liquid supplying unit; a controlling unit configured to control a supplying rate of the acoustic matching liquid; and a scanning unit, wherein the controlling unit is configured to reduce the supply of the acoustic matching liquid into the liquid vessel when the reception transducer array detects an acoustic wave.

42 Claims, 9 Drawing Sheets

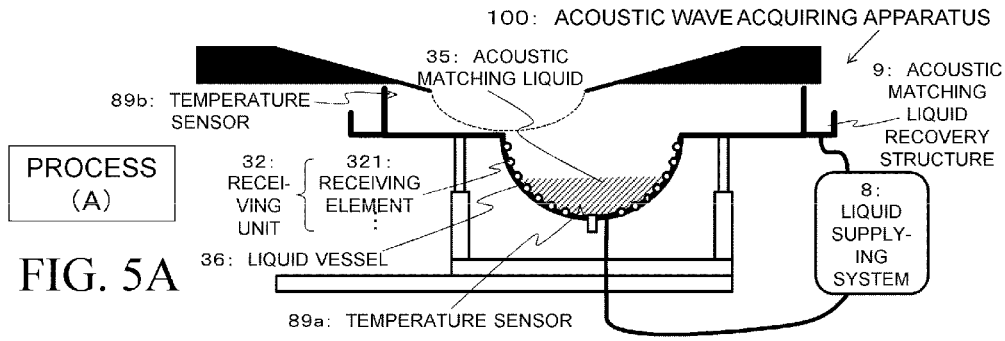
FIG. 5A PROCESS (A)
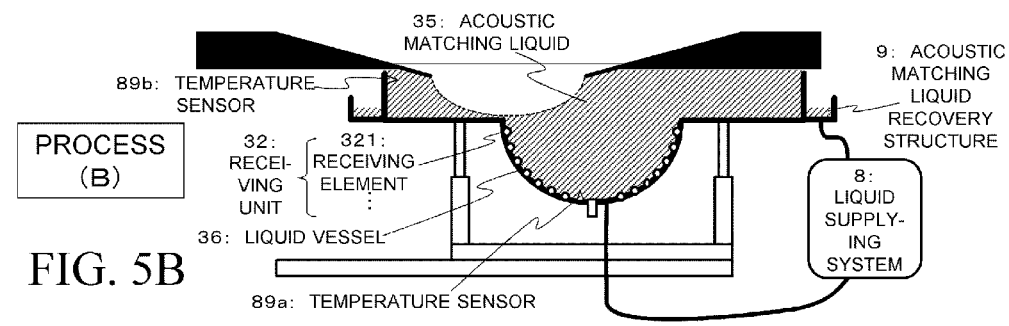
FIG. 5B PROCESS (B)
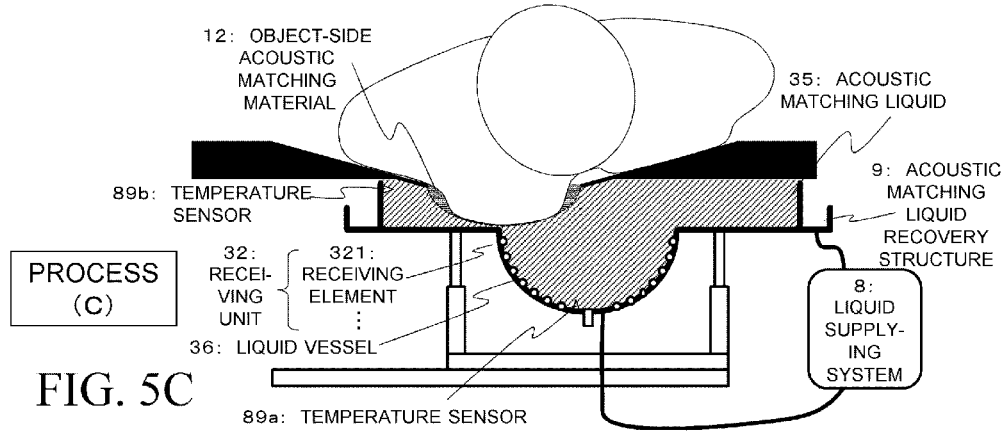
FIG. 5C PROCESS (C)
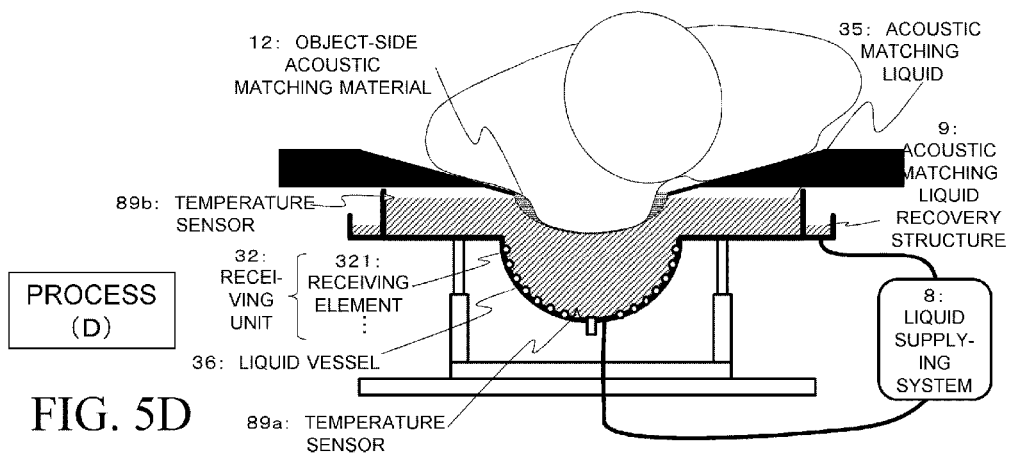
FIG. 5D PROCESS (D)

ACOUSTIC WAVE RECEIVING APPARATUS AND CONTROL METHOD THEREOF

BACKGROUND OF THE INVENTION

Field of the Invention

The present invention relates to an acoustic wave receiving apparatus and a control method thereof.

Description of the Related Art

In recent years, photoacoustic imaging apparatuses which perform imaging of the inside of a living organism using a photoacoustic effect are being researched and developed. A photoacoustic imaging apparatus irradiates the inside of a living organism with pulsed laser light (laser pulses) which are emitted for a short time. In addition, the photoacoustic imaging apparatus generates an image indicating a characteristic information distribution inside an object using an electrical signal obtained by receiving, with a probe, an acoustic wave (a photoacoustic wave) generated when tissue of the living organism having absorbed energy of the pulsed laser light expands due to heat generation.

Photoacoustic imaging apparatuses are researched and developed as, for example, apparatuses for observing a human breast for the purpose of early detection of breast cancer. An example of a specific configuration is disclosed in Japanese Patent Application Laid-open No. 2015-205041.
Patent Literature 1: Japanese Patent Application Laid-open No. 2015-205041

SUMMARY OF THE INVENTION

Generally, with a photoacoustic imaging apparatus, an acoustic matching liquid is arranged between an object section and a probe. The acoustic matching liquid is a material having an acoustic impedance close to those of the object section and the probe. An acoustic matching material reduces reflection at an interface present between an object section and a probe when an acoustic wave propagates from the object section to the probe.

Furthermore, when relative positions of the probe and the object section change, a liquid (an acoustic matching liquid) is favorably used as the acoustic matching material. Accordingly, a space between the probe and the object section can be filled regardless of shapes of the probe and the object section and a scan trajectory of the probe.

On the other hand, when an acoustic matching liquid is supplied to a liquid vessel constituting an acoustic wave propagation path between the object and the probe in order to store the acoustic matching liquid, bubbles created in a flow channel related to the supply of liquid may become intermingled with the acoustic matching liquid stored in the liquid vessel. Once the bubbles adhere to the probe or an object holding member, propagation of an acoustic wave from the object is inhibited. As a result, a decline in image quality such as an occurrence of noise or an artifact in an obtained image occurs. Moreover, the problem related to an acoustic matching liquid and bubbles described above is not limited to photoacoustic imaging apparatuses and is shared by ultrasound echo apparatuses.

The present invention has been made in consideration of the problems described above. An object of the present invention is to reduce an effect of bubbles during imaging of an object using acoustic waves.

The present invention provides an acoustic wave receiving apparatus, comprising:

a sheet-shaped holding member configured to hold with one surface thereof an object and to cause an acoustic wave propagated from the object to propagate to a side of the other surface;

a reception transducer array including a plurality of receiving elements configured to receive an acoustic wave propagated from the object via the holding member and to convert the acoustic wave into an electrical signal;

a liquid vessel to which the reception transducer array is fixed and configured to store an acoustic matching liquid so that the object and the reception transducer array are acoustically coupled to each other;

a liquid supplying unit configured to supply the acoustic matching liquid to the inside of the liquid vessel;

a controlling unit configured to control a supplying rate of the acoustic matching liquid to be supplied into the liquid vessel;

a scanning unit configured to change relative positions of the object, the receiving elements, and the liquid vessel; and an information generating unit configured to generate characteristic information on the object using the electrical signal, wherein the liquid supplying unit is configured to be controlled by the controlling unit so that the supplying rate for a first period of time when the reception transducer array is open to receiving the reflected acoustic wave is lower than that for a second period of time when the reception transducer array is not open to receiving the reflected acoustic wave.

The present invention also provides a control method of an acoustic wave receiving apparatus including a reception transducer array provided with a plurality of receiving elements, a liquid vessel, and a liquid supplying unit supplying an acoustic matching liquid to the liquid vessel, the control method comprising:

receiving an acoustic wave propagating from an object via a holding member and converting the acoustic wave into an electrical signal;

supplying the acoustic matching liquid into the liquid vessel;

controlling a supplying rate of the acoustic matching liquid to be supplied into the liquid vessel;

generating characteristic information on the object using the electrical signal; and wherein the controlling is performed such that the supplying rate for a first period of time when the transducer is open to receiving the reflected acoustic wave is lower than that for second period of time when the transducer is not open to receiving the reflected acoustic wave.

According to the present invention, an effect of bubbles during imaging of an object using acoustic waves can be reduced.

Further features of the present invention will become apparent from the following description of exemplary embodiments with reference to the attached drawings.

BRIEF DESCRIPTION OF THE DRAWINGS

FIGS. 5A to 5D are diagrams showing an acoustic matching liquid supply sequence (from start to first measurement);

DESCRIPTION OF THE EMBODIMENTS

Figure 1:
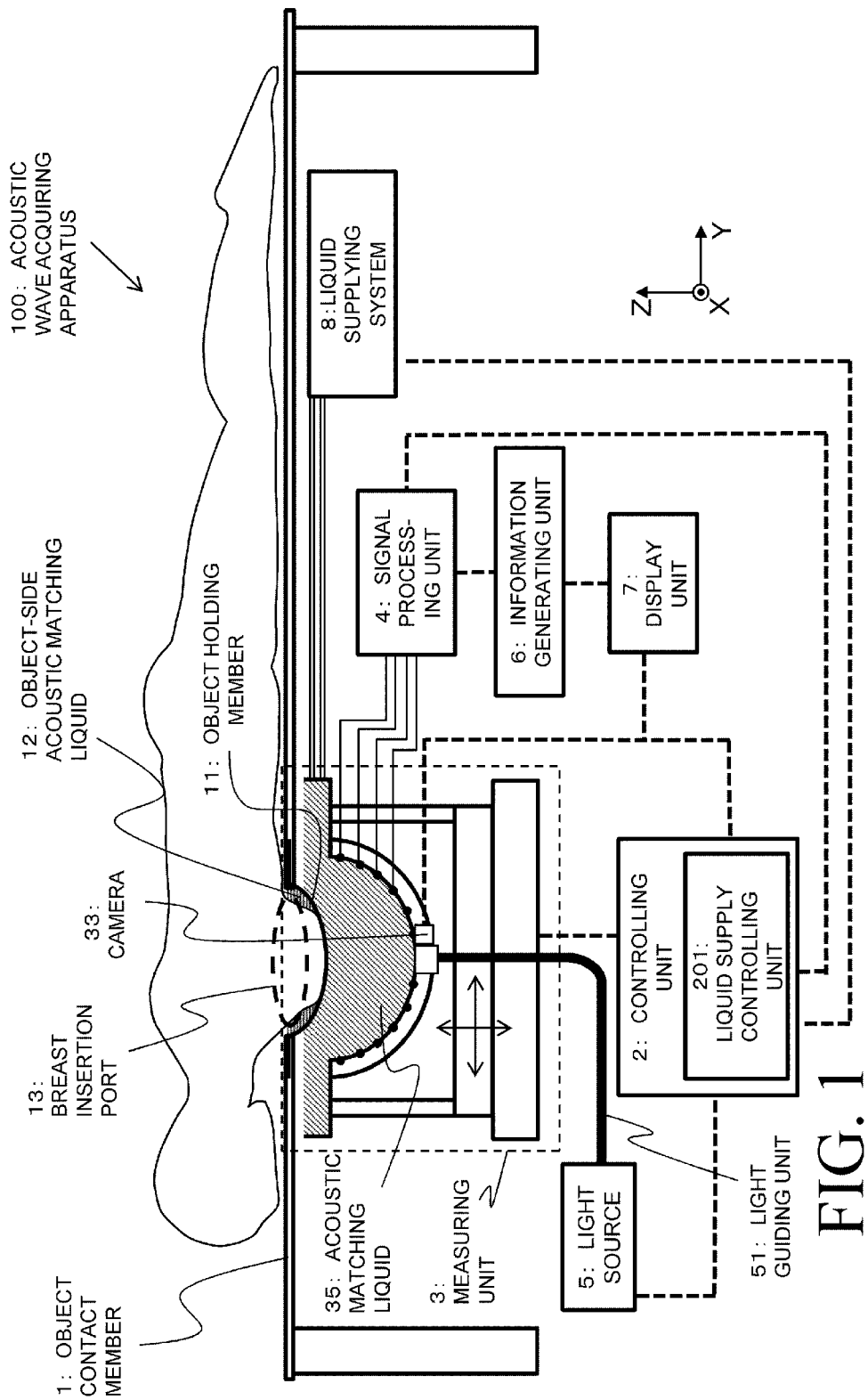
FIG. 1 is a block diagram of a photoacoustic imaging apparatus according to the present invention.

Hereinafter, preferred embodiments of the present invention will be described with reference to the drawings. However, it is to be understood that dimensions, materials, shapes, relative arrangements, and the like of components described below are intended to be changed as deemed appropriate in accordance with configurations and various conditions of apparatuses to which the present invention is to be applied. Therefore, the scope of the present invention is not intended to be limited to the embodiments described below.

The present invention relates to a technique for detecting an acoustic wave propagated from an object and generating and acquiring characteristic information on the inside of the object. Accordingly, the present invention can be considered an object information acquiring apparatus or a control method thereof, or an object information acquiring method and a signal processing method. The present invention can also be considered a program that causes an information processing apparatus including hardware resources such as a CPU and a memory to execute these methods or a computer-readable non-transitory storage medium storing the program.

The object information acquiring apparatus according to the present invention includes an apparatus utilizing a photoacoustic effect in which an acoustic wave generated inside an object by irradiating the object with light (an electromagnetic wave) is received and characteristic information on the object is acquired as image data. In this case, characteristic information refers to information on a characteristic value corresponding to each of a plurality of positions inside the object which is generated using a received signal obtained by receiving a photoacoustic wave.

Characteristic information (photoacoustic characteristic information) derived from an electrical signal (a photoacoustic signal) acquired by photoacoustic measurement is a value reflecting an absorption rate of optical energy. For example, characteristic information includes a generation source of acoustic waves generated by light irradiation, initial sound pressure inside an object, an optical energy absorption density or an absorption coefficient derived from initial sound pressure, or a concentration of substances constituting tissue. In addition, a distribution of oxygen saturation can be calculated by obtaining a concentration of oxygenated hemoglobin and a concentration of deoxygenated hemoglobin as concentrations of substances. Furthermore, a glucose concentration, a collagen concentration, a melanin concentration, a volume fraction of fat or water, and the like are also obtained.

The object information acquiring apparatus according to the present invention includes an apparatus using ultrasound echo technology which involves transmitting an ultrasound wave to an object, receiving a reflected wave (an echo wave) that is reflected inside the object, and acquiring object information as image data. Characteristic information (ultrasound characteristic information) derived from an electrical signal (an ultrasound echo signal) acquired by an ultrasound echo apparatus is information reflecting a difference in acoustic impedances among tissues inside an object.

A two-dimensional or three-dimensional characteristic information distribution is obtained based on characteristic information at each position in the object. Distribution data may be generated as image data. Characteristic information may be obtained as distribution information at respective positions inside the object instead of as numerical data. In other words, distribution information such as a distribution of initial sound pressure, a distribution of energy absorption density, a distribution of absorption coefficients, and a distribution of oxygen saturation may be obtained. In addition, an acoustic impedance distribution, distribution information representing blood flow, and the like may also be generated. Since information based on acoustic waves is visualized as described above, the present invention can also be considered an acoustic imaging apparatus, a control method thereof, or a program thereof.

An acoustic wave according to the present invention is typically an ultrasound wave and includes an elastic wave which is also referred to as a sonic wave or an acoustic wave. An electrical signal transformed from an acoustic wave by a probe or the like is also referred to as an acoustic signal. However, descriptions of an ultrasound wave and an acoustic wave in the present specification are not intended to limit a wavelength of such elastic waves. An acoustic wave generated by a photoacoustic effect is referred to as a photoacoustic wave or an optical ultrasound wave. An electrical signal derived from a photoacoustic wave is also referred to as a photoacoustic signal. In addition, an electrical signal derived from an echo wave created when a transmitted ultrasound wave is reflected by an object is also referred to as an ultrasound echo signal.

In any of a case where an apparatus according to the present invention receives photoacoustic waves, a case where the apparatus receives ultrasound wave echoes, and a case where the apparatus receives both photoacoustic waves and ultrasound wave echoes, the fact remains that the apparatus receives acoustic waves. Therefore, an apparatus according to the present invention can be called an acoustic wave receiving apparatus. The present invention can also be considered a control method of such an acoustic wave receiving apparatus.

First Embodiment (Overall Configuration of Apparatus)

In the present embodiment, a photoacoustic imaging apparatus will be described as an example of an acoustic wave acquiring apparatus 100. FIG. 1 is a block diagram of a photoacoustic imaging apparatus according to the present invention.

An examinee assumes a face-down posture on an object contact member 1, allows a breast to droop and inserts the breast into a breast insertion port 13 which constitutes an opening of the object contact member 1, and brings the breast into contact with an object holding member 11.

A measuring unit 3 irradiates the breast held by the object holding member 11 with optical energy from a light source 5 and receives a photoacoustic wave generated by the breast. Moreover, during photoacoustic measurement, an acoustic matching liquid 35 is arranged on a path between the measuring unit 3 and the object holding member 11.

A controlling unit 2 controls intensity of irradiated light, timings of light irradiation and acoustic wave reception, scanning of a receiving unit to be described later, and the like. In addition, the controlling unit 2 at least includes a liquid supply controlling unit 201. During apparatus control, the liquid supply controlling unit 201 performs control of supply, discharge, and circulation of the acoustic matching liquid 35 and control of scanning related to supply of the acoustic matching liquid 35. However, the controlling unit 2 and the liquid supply controlling unit 201 need not be strictly separated from each other and, for example, may be configured as program modules that run on a same computer or may realize desired functions by cooperating with each other in a distributed manner.

A received acoustic wave is subjected to amplification and AD conversion by a signal processing unit 4 and becomes a photoacoustic signal. An information generating unit 6 uses a photoacoustic signal to generate and acquire characteristic information on the inside of an object. Typically, the information generating unit 6 generates a two-dimensional or three-dimensional photoacoustic image. A display unit 7 displays a generated photoacoustic image and an image captured by a camera 33.

(Object Holding Member)

The object holding member 11 has a shape and material which enable a breast to be readily held. For example, a sheet-shaped member with a bowl shape can be used. The object holding member 11 need not have a perfect spherical surface and need only have a shape matching shapes of a breast and an axillary region. The object holding member 11 favorably has a plurality of switchable shapes or sizes in accordance with breast sizes. Accordingly, an occurrence of a gap between the breast and the object holding member 11 can be suppressed. Moreover, since the presence of the object holding member 11 stabilizes the shape of the object, the object holding member 11 is effective in improving accuracy and reducing processing time with respect to measurement and image generation. However, creation and adherence of bubbles occur regardless of the presence or absence of the object holding member 11, hence, the effects of the present invention are exhibited even when the object holding member 11 is not provided.

Since the object holding member 11 is to be liquid-tightly attached to the object contact member 1, the object holding member 11 has a flange shape in a periphery of a bowl shape and a portion where the bowl shape and the flange shape overlap each other is made smooth so that the examinee can come into contact with the portion in a painless manner. When attaching the flange-shaped portion to the object contact member 1, for example, a method of sandwiching a ring-shaped seal material between the object contact member 1 and the flange-shaped portion and fixing the flange-shaped portion with screws may be used. When the flange-shaped portion is made of resin or the like and strength thereof is insufficient, the flange-shaped portion may be attached by further reinforcing the seal material and the flange shape with a metallic ring-shaped member from above and sandwiching the flange-shaped portion.

Favorable characteristics of the object holding member 11 include having a thin sheet shape (typically, with a thickness of 0.01 to 0.5 mm) so as to readily transmit acoustic waves, being transparent so as to transmit light, and being strong enough to withstand weight of the examinee. Polyethylene terephthalate (PET) is a material having such characteristics. When the object holding member 11 transmits an acoustic wave, the object holding member 11 holds the object with one surface and enables an acoustic wave propagated from the object to propagate to the side of the other surface. In addition, a sheet-shaped member which deforms in accordance with a shape of an object part due to the weight of the examinee can also be used.

A space between the object holding member 11 and the breast is filled with an object-side acoustic matching liquid 12 which acoustically couples the object holding member 11 and the breast with each other and enables an acoustic wave to be transmitted more readily. Examples of the object-side acoustic matching liquid 12 include water and castor oil. In addition, a gel or the like may also be used.

It is also favorable to treat a convex-side surface of the object holding member 11 so as to suppress and reduce adherence of bubbles. For example, when the acoustic matching liquid is water, a silane coupling treatment or a titanium oxide treatment thin enough to prevent transmission of light from being suppressed may be applied to the convex-side surface of the object holding member.

The measuring unit 3 adjusts a position in a Z-direction in accordance with a size of the object holding member 11 and performs a two-dimensional or three-dimensional scan at a Z-direction position with highest receiving sensitivity. Examples of a method of determining a size (or a type) of the object holding member 11 includes a method of creating a notched shape indicating a size on the object holding member 11 and automatically detecting the size with a detecting unit such as a switch or a sensor (not illustrated) provided on the measuring unit 3. Alternatively, a barcode or the like may be affixed to the object holding member 11 in advance and a type of the object holding member 11 may be detected using an image taken by the camera 33. Automatically detecting the type of the object holding member 11 eliminates the trouble of having a person manually input the type and, at the same time, eliminates mistakes due to erroneous input.

(Light Source)

The light source 5 supplies optical energy to the object and causes the object to generate a photoacoustic wave. When the object is a living organism, light with a specific wavelength which is absorbed by a specific component among components constituting the breast is irradiated from the light source 5. The light source may be integrally provided with the photoacoustic apparatus according to the present embodiment or the light source may be separated and provided as an independent body. As the light source, a pulsed light source capable of generating pulsed light in the order of several nanoseconds to several hundred nanoseconds as irradiated light is favorable. Specifically, in order to efficiently generate photoacoustic waves, a pulse width of around 10 to 100 nanoseconds is used.

As the light source, a laser is favorable since a high output is obtained. However, a flash lamp or a light-emitting diode may also be used. As the laser, various lasers such as a solid-state laser, a gas laser, a fiber laser, a dye laser, and a semiconductor laser can be used. Timings, waveforms, intensity, and the like of irradiation are controlled by a light source control unit (not shown). In the present invention, a wavelength of the used light source is desirably a wavelength which enables light to propagate to the inside of a breast. Specifically, a desirable wavelength is at least 500 nm and not more than 1200 nm. In addition, by using a wavelength variable laser capable of switching among a plurality of wavelengths, substance concentration information such as oxygen saturation and glucose concentration can be acquired.

(Measuring Unit Configuration)

Figure 2:
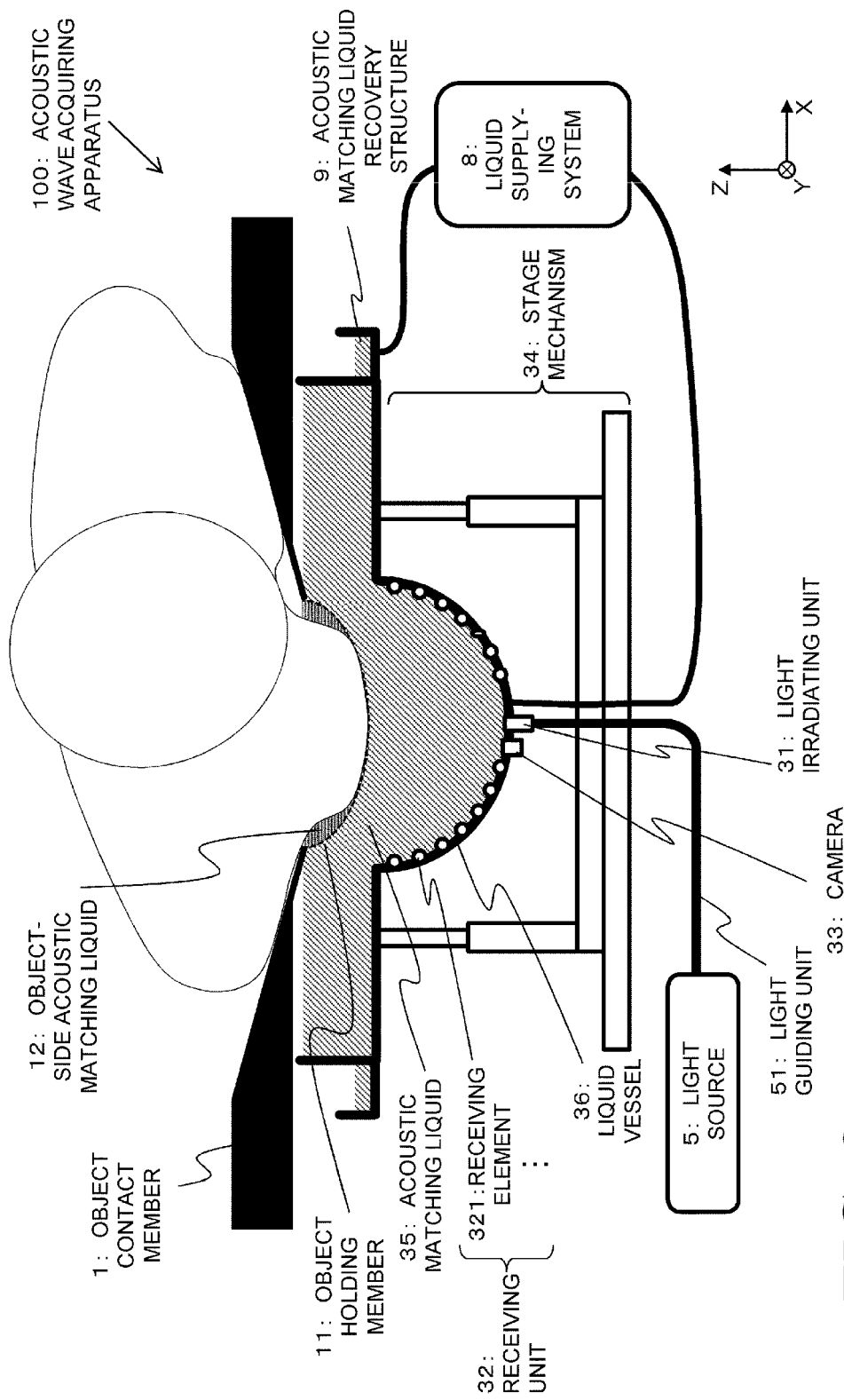
FIG. 2 is a conceptual diagram centered on a measuring unit of a photoacoustic imaging apparatus.

FIG. 2 is a conceptual diagram of a measuring unit according to the present invention. The measuring unit includes a light irradiating unit 31 which irradiates a breast with laser light guided using a light guiding unit 51 from the light source 5, two or more receiving elements 321 which receive ultrasound waves generated at and propagated from the breast, the camera 33 for observing a held state of the breast, and a stage mechanism 34 which two-dimensionally moves the light irradiating unit 31 in an XY plane. The light irradiating unit 31 is arranged at a position opposing the object section (breast).

The receiving unit 32 includes a reception transducer array which supports the plurality of receiving elements 321. In addition, the receiving unit 32 receives a photoacoustic wave generated at and propagated from the breast due to a photoacoustic effect with the reception transducer array. The reception transducer array is, for example, a supporter made of metal or resin which is strong enough to prevent deformation due to scanning. The number of receiving elements and an arrangement pattern thereof on the reception transducer array are not limited. However, by arranging the receiving elements on a hemispherical or bowl-shaped supporter so that directions with high receiving sensitivity of the respective receiving elements concentrate, a high sensitivity region with high resolution can be formed.

For example, an image obtained by the camera 33 can be used to confirm whether or not the breast is in close contact with the object holding member by image analysis or visual confirmation by a user.

The receiving unit 32 includes a liquid vessel 36. The acoustic matching liquid 35 is stored inside the liquid vessel 36 and the liquid vessel 36 and the reception transducer array are fixed to each other. Accordingly, a path between the receiving unit 32 and the object holding member 11 is filled with the acoustic matching liquid 35. In order to acoustically couple the reception transducer array and the object holding member with each other, water or the like of which an acoustic impedance is close to that of a human body than air is used as the acoustic matching liquid 35. Moreover, when the acoustic matching liquid 35 is water, it also favorable to mix a surfactant such as soap into water in order to increase wettability and suppress or reduce the adherence of bubbles.

A plurality of receiving elements 321 which receive photoacoustic waves are arranged in the receiving unit 32. In this case, by arranging the receiving elements 321 so that a receiving surface (a directional axis) of at least a part of the receiving elements 321 is at a different angle, an object part can be measured from a different direction and image quality improves. In a more preferable embodiment, the plurality of receiving elements may be arranged so that receiving surfaces of the receiving elements face a center of the hemispherical liquid vessel 36.

The stage mechanism 34 is a triaxial stage mechanism capable of three-dimensional scanning in XYZ directions. A triaxial stage is constituted by a combination of a linear guide (not shown), a feed screw mechanism (not shown), and a motor (not shown). Any kind of scanning unit may be used as long as a relative positional relationship between the receiving unit including the receiving elements and the object holding member is variable. A scan trajectory is not particularly limited. For example, in the case of an object with a protruding surface such as a breast, a spiral scan with a trajectory from an outer peripheral part toward an inner peripheral part or from a central part toward an outer side is preferable. Otherwise, scans according to modifications of the present embodiment include a combination of a plurality of circular scans having mutually different diameters, a boustrophedon scan, a raster scan, a reciprocal scan, and a meander scan.

Moreover, in the present embodiment, the receiving elements 321 are scanned together with the liquid vessel 36. However, only the receiving elements or only an element array on which the receiving elements are arranged may be moved without moving the liquid vessel 36. Such a configuration can be realized by storing the acoustic matching liquid in a water tank-like liquid vessel and moving receiving elements positioned relatively low inside the water tank. In this case, a spill amount of the acoustic matching liquid is small since the liquid vessel does not move. However, since a liquid amount may decrease due to scanning of the receiving elements, a body motion of an examinee, evaporation, and the like, the method according to the present invention is effective.

(Receiving Element)

The receiving element 321 detects an acoustic wave, converts the acoustic wave into an electrical signal, and outputs the electrical signal. Any kind of element including an element using a piezoelectric phenomenon, an element using optical resonance, and an element using a change in capacity may be used as long as an acoustic wave can be detected. In the present embodiment, the receiving element 321 is arranged in plurality and each receiving element is arranged so that a direction in which the receiving element has highest receiving sensitivity differs from other receiving elements. Since the use of such multi-dimensionally arranged elements enables acoustic waves to be simultaneously detected at a plurality of locations, measurement time can be shortened.

(Receiving Unit, Liquid Vessel)

The receiving unit 32 is favorably configured so that the plurality of receiving elements 321 are arranged on a closed curved surface surrounding the breast. However, it is difficult to arrange the plurality of receiving elements 321 on all closed curved surfaces surrounding the object section (breast). In consideration thereof, the plurality of receiving elements 321 are favorably arranged on a hemispherical surface. The liquid vessel 36 is shaped so that the acoustic matching liquid 35 can be stored between the object holding member 11 and the receiving unit 32. In addition, a relative positional relationship of the liquid vessel 36 with the object part can be changed. For example, a scanning unit such as a stage for XY-scanning the liquid vessel 36 may be provided. In this manner, when using the receiving unit 32 in which the liquid vessel 36 and the reception transducer array are fixed, the scanning unit integrally moves the entire receiving unit 32.

FIG. 2 shows the receiving unit 32 including the liquid vessel 36 satisfying the conditions described above. The liquid vessel 36 has a shape constituted by a hemispherical portion and a portion extending in an outer peripheral direction from the hemispherical portion. The liquid vessel 36 may be integrally molded or created by combining a plurality of parts.

Favorably, the light irradiating unit 31 is further arranged in the liquid vessel 36. Accordingly, since a relationship between a receiving position of acoustic waves and an irradiating position of light can be kept constant, more uniform photoacoustic wave information can be acquired. An irradiation area over which the breast can be irradiated is limited by the American National Standards Institute (ANSI) standard. Therefore, while increasing irradiation intensity and an irradiation area is favorable in order to increase the amount of light propagating to the inside of the breast, the irradiation area is limited from the perspectives of cost and the like of the light source. In addition, utilization efficiency of light intensity is low even when a region with low receiving sensitivity is irradiated with light. For this reason, it is not efficient to irradiate light over the entire breast. In other words, since it is efficient to irradiate light only on a high sensitivity region of the receiving unit 32 constituted by the plurality of receiving elements 321, the light irradiating unit 31 desirably moves together with the receiving unit 32.

(Light Guiding Unit)

Light irradiated from the light source 5 shown in FIG. 1 is guided to the object while being processed into a desired light distribution shape by the light guiding unit 51. Typically, an optical part such as a lens, a mirror, and a diffuser plate can be used as the light guiding unit 51. In addition, an optical fiber or a bundled optical fiber which is a bundle of optical fibers, an optical waveguide such as an articulating arm created by incorporating a mirror or the like into a lens barrel, and the like can also be used for light propagation. These parts are also considered the light guiding unit 51. Any kind of optical part may be used as long as light emitted by the light source irradiates the breast in a desired shape. Moreover, spreading light over a relatively wide area is more favorable than focusing light with a lens from the perspective of expanding a diagnostic area with respect to the object. When desired pulsed light can be directly emitted to the breast from the light source 5 and the light source 5 can be scanned together with the liquid vessel 36, the photoacoustic apparatus need not include the light guiding unit 51.

(Signal Processing Unit)

The signal processing unit 4 is constituted by an AD conversion circuit for digitizing an analog electrical signal, an amplifier which amplifies an electrical signal, and the like. A digital electrical signal time-sequentially obtained for each receiving element is output to and stored in a memory (not shown).

(Controlling Unit, Information Generating Unit)

As the controlling unit 2 and the information generating unit 6, an information processing apparatus (for example, a PC or a work station) which includes computing resources such as a processor, a memory, and a communication apparatus and which operates in accordance with a program is preferable. The controlling unit 2 outputs a control signal to each block in the apparatus based on input information from the user and measurement values from various sensors. A portion which realizes circulation, supply and discharge, and temperature adjustment of the acoustic matching liquid 35, scanning of the receiving unit in accordance therewith, and the like in the controlling unit 2 may particularly be referred to as the liquid supply controlling unit 201.

The controlling unit 2 and the information generating unit 6 may be configured as program modules which realize respective functions in a same information processing apparatus or may respectively operate in separate information processing apparatuses and execute information processing related to the photoacoustic imaging apparatus by cooperating with each other. This description also applies to a relationship between the controlling unit 2 and the liquid supply controlling unit 201. An input apparatus (for example, a mouse, a keyboard, or a touch panel) of an information processing apparatus may be used as an input unit of the photoacoustic imaging apparatus. Items input from the input unit include a range of a region of interest (ROI) of the object, measurement parameters, and desired image quality.

(Display Unit)

The display unit 7 displays generated image data. Any display apparatus including a liquid crystal display and an organic EL display can be used as the display unit 7. The display unit 7 may be provided together with the photoacoustic imaging apparatus or may be provided separately from the photoacoustic imaging apparatus.

(Liquid Supplying System)

Figure 3:
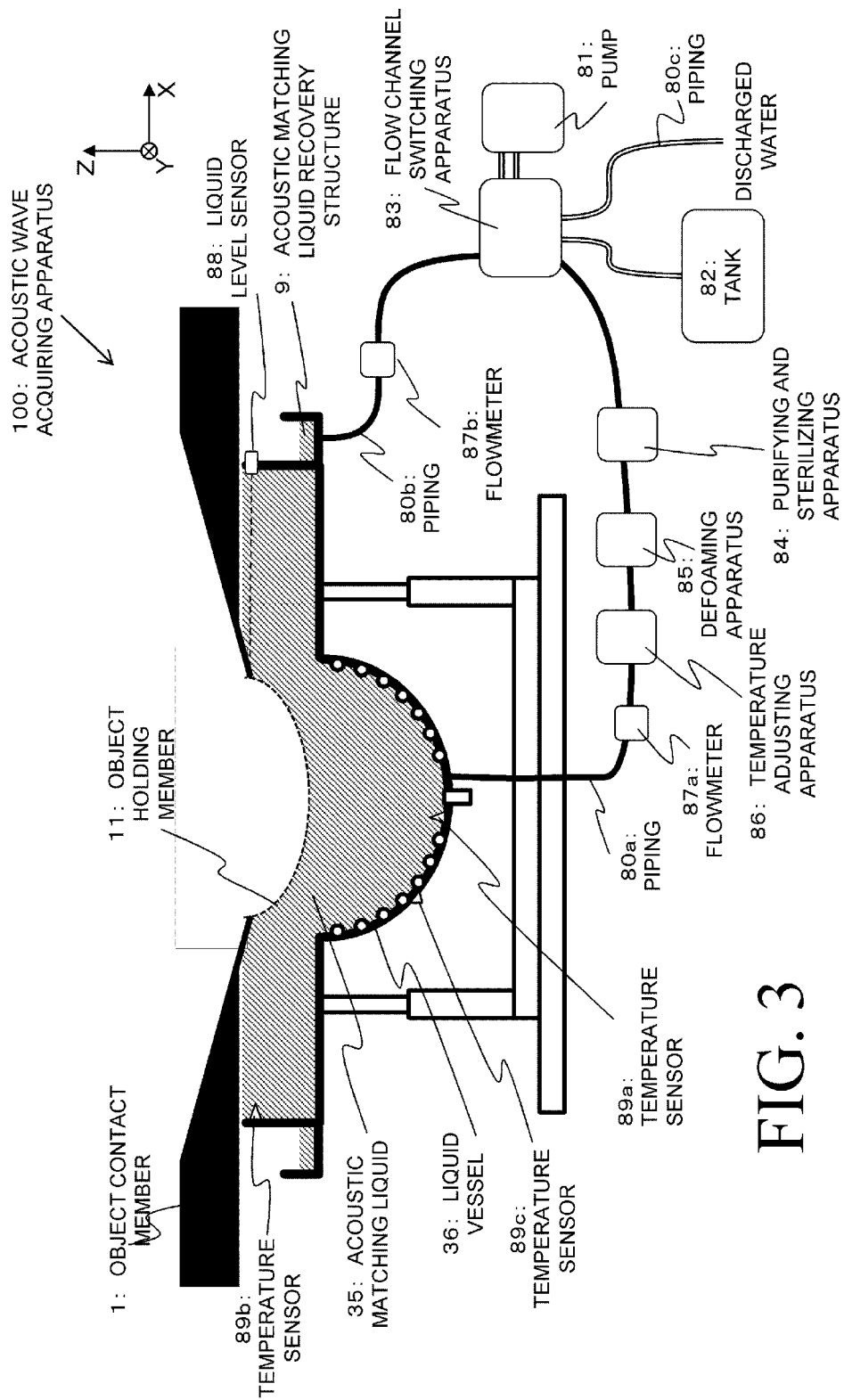
FIG. 3 is a conceptual diagram of a liquid supplying system of a photoacoustic imaging apparatus.

FIG. 3 is a diagram showing an example of a configuration of a liquid supplying system 8 according to the present invention. The liquid supplying system 8 includes a pump 81, a tank 82, a flow channel switching apparatus 83, a purifying and sterilizing apparatus 84, a defoaming apparatus 85, a temperature adjusting apparatus 86, flowmeters 87a and 87b, pipings 80a and 80b, a liquid level sensor 88, and temperature sensors 89a, 89b, and 89c. The liquid supplying system 8 corresponds to the liquid supplying unit according to the present invention.

The acoustic matching liquid 35 is stored in the tank 82 and is sent by the pump 81 via the flow channel switching apparatus 83 to the purifying and sterilizing apparatus 84 which purifies and sterilizes the acoustic matching liquid 35. Subsequently, the acoustic matching liquid 35 travels through the piping 80a while passing the defoaming apparatus 85 which removes air and bubbles dissolved in the liquid (in other words, performs defoaming and degassing) and the temperature adjusting apparatus 86 which heats the acoustic matching liquid 35, and is supplied to the liquid vessel 36.

a supplying rate and supplied amount of the acoustic matching liquid 35 supplied into the liquid vessel 36 are measured by the flowmeter 87a and controlled based on a measured rate. The liquid level sensor 88 confirms whether or not the acoustic matching liquid 35 supplied to the inside of the liquid vessel 36 is stored at a sufficient liquid level. When the liquid level drops, a measurement error or a warning is output to the display unit 7.

When the acoustic matching liquid 35 is further supplied, the acoustic matching liquid 35 flows out from between an upper part of the liquid vessel 36 and the object contact member. Subsequently, the acoustic matching liquid 35 flows out from the piping 80b via an acoustic matching liquid recovery structure 9 constructed in an outer periphery of the liquid vessel 36. An amount of the acoustic matching liquid 35 which flows out from the piping 80b is measured by the flowmeter 87b and used to manage and control an inflow amount and an outflow amount of the acoustic matching liquid 35 to and from the liquid vessel 36.

The pump 81 for moving the acoustic matching liquid 35 may be provided in plurality when necessary. A type of the pump is not particularly limited. For example, since a gear pump, a tube pump, or the like can move the acoustic matching liquid 35 in both supplying and discharging directions by reversing a motor, the number of switching operations by the flow channel switching apparatus 83 can be reduced. The flow channel switching apparatus 83 selects piping for feeding the acoustic matching liquid 35 to the pump and piping for feeding out the acoustic matching liquid 35 from the pump. The flow channel switching apparatus 83 can be configured by combining electromagnetic valves or the like.

The purifying and sterilizing apparatus 84 suppresses putrefaction of the acoustic matching liquid 35 and propagation of organic substances such as algae and lichen in the liquid. For example, an ultraviolet sterilizer can be used.

The generation of bubbles in the acoustic matching liquid 35 affects reception of acoustic waves and causes noise or artifacts in an image. For this reason, the defoaming apparatus 85 removes bubbles and dissolved gas components. However, there may be cases where, for example, air having entered the piping 80*a* when the acoustic matching liquid 35 in the liquid vessel 36 is completely emptied returns to the liquid vessel 36 by a movement of the piping 80*a* due to scanning during measurement. As described above, the possibility of bubbles entering the liquid vessel 36 cannot be completely eliminated. In consideration thereof, in the present invention, in order to reduce the bubbles flowing into the liquid vessel 36 from the piping 80*a* during measurement, supply of the acoustic matching liquid 35 is suppressed or reduced as will be described later. More specifically, the liquid supply controlling unit 201 favorably performs control so that the supplying rate for a first period of time when the reception transducer array is open to receiving the reflected acoustic wave is lower than that for a second period of time when the reception transducer array is not open to receiving the reflected acoustic wave so as not to introduce any bubbles substantially into the liquid vessel.

The acoustic matching liquid 35 defoamed and degassed by the defoaming apparatus 85 is sent to the temperature adjusting apparatus 86. Since the examinee feels discomfort when the acoustic matching liquid 35 is excessively cold, the acoustic matching liquid 35 is heated to around body temperature by the temperature adjusting apparatus 86. As the temperature adjusting apparatus 86 which changes the temperature of the acoustic matching liquid 35, a heater which increases the temperature of liquids or the like can be used. Alternatively, an air conditioner for lowering air temperature may be provided.

In addition, information necessary when forming an image from an obtained acoustic signal includes a sound velocity of the acoustic matching liquid 35. Since the sound velocity of the acoustic matching liquid 35 changes according to the temperature, the temperature of the acoustic matching liquid 35 must be determined. Favorably, the temperature of the acoustic matching liquid 35 is constant and there is no temperature unevenness. In order to effectively eliminate temperature unevenness, the acoustic matching liquid 35 stored in the liquid vessel 36 is stirred by scanning of the receiving unit or by a stirrer.

However, depending on a history of heating processes and cooling processes, uniformization and equalization of the temperature of the stored acoustic matching liquid by temperature adjust may lower solubility of the acoustic matching liquid in air and, in turn, cause dissolved gas to turn into bubbles.

In addition, since stirring the acoustic matching liquid also constitutes an act of microscopically moving a gas-liquid interface into the liquid, a possibility of promoting mixing of bubbles into the acoustic matching liquid increases. The present invention is also applicable to an acoustic wave receiving apparatus provided with a temperature adjusting apparatus or a stirring apparatus which promotes mixing of bubbles attributable to a liquid supply system.

In the configuration according to the present invention, when the heated acoustic matching liquid 35 is sent into the liquid vessel 36, the acoustic matching liquid 35 dissipates heat via the object contact member 1 and the liquid vessel 36. Therefore, the temperature of the acoustic matching liquid 35 which is present near the object contact member 1 or an inner peripheral wall surface of the liquid vessel 36 tends to drop. On the other hand, since the object present via the object holding member 11 is at body temperature, the object acts as a heat source. Therefore, the temperature of the acoustic matching liquid 35 which is present near the object holding member 11 is less likely to drop. As described above, the presence of a heat source and a heat dissipating section inside the acoustic matching liquid 35 causes temperature unevenness to occur.

Therefore, in order to maintain the acoustic matching liquid 35 in the liquid vessel 36 at around body temperature without creating temperature unevenness, favorably, the acoustic matching liquid 35 heated to around body temperature is continuously supplied to the liquid vessel 36. The temperature of the acoustic matching liquid 35 inside the liquid vessel 36 is measured by the temperature sensor 89*a* near an inflow section of the acoustic matching liquid 35 in a lower part of the liquid vessel 36 and the temperature sensor 89*b* near an outflow section of the acoustic matching liquid 35 above the liquid vessel 36.

The measured temperatures can be used for temperature control by the liquid supply controlling unit 201. A simple method involves confirming whether or not the temperatures measured by the temperature sensors 89*a* and 89*b* are temperatures sent in advance and are in a steady state. In addition, by adopting the fact that the temperatures are in a steady state as a condition upon starting measurement, a value of acoustic impedance necessary when forming an image becomes accurate and, consequently, obtained image quality is improved.

Furthermore, for example, by confirming that a value of the temperature sensor 89*c* attached to the outside of the liquid vessel 36 becomes steady, temperatures including an apparatus part to which the acoustic matching liquid 35 comes into contact can be confirmed to be in a steady state. When temperatures including the apparatus part to which the acoustic matching liquid 35 comes into contact are in a steady state, even when supply of the acoustic matching liquid 35 is stopped so that bubbles are not introduced from the piping 80*a* during measurement, a temperature variation during this period can be reduced.

The tank 82 has a capacity large enough to store all of the acoustic matching liquid 35 flowing through the liquid supplying system 8 including the liquid vessel 36 and includes a supply port and a discharge port (both not shown). In addition, the purifying and sterilizing apparatus 84, the defoaming apparatus 85, and the temperature adjusting apparatus 86 may be installed inside the tank 82. Moreover, the pump 81, the tank 82, the flow channel switching apparatus 83, the purifying and sterilizing apparatus 84, the defoaming apparatus 85, and the temperature adjusting apparatus 86 can be optimized by changing a connection sequence thereof when necessary.

In addition, the acoustic matching liquid need not necessarily be circulated and, for example, a configuration may be adopted in which tap water or the like is heated and supplied and discharged water is not reused. Measurement values obtained by the flowmeters 87*a* and 87*b*, the liquid level sensor 88, and the temperature sensors 89*a* and 89*b* are transmitted to the controlling unit 2 and used to control each block.

(Acoustic Matching Liquid Supply Sequence)

Figures 4A, 4B:
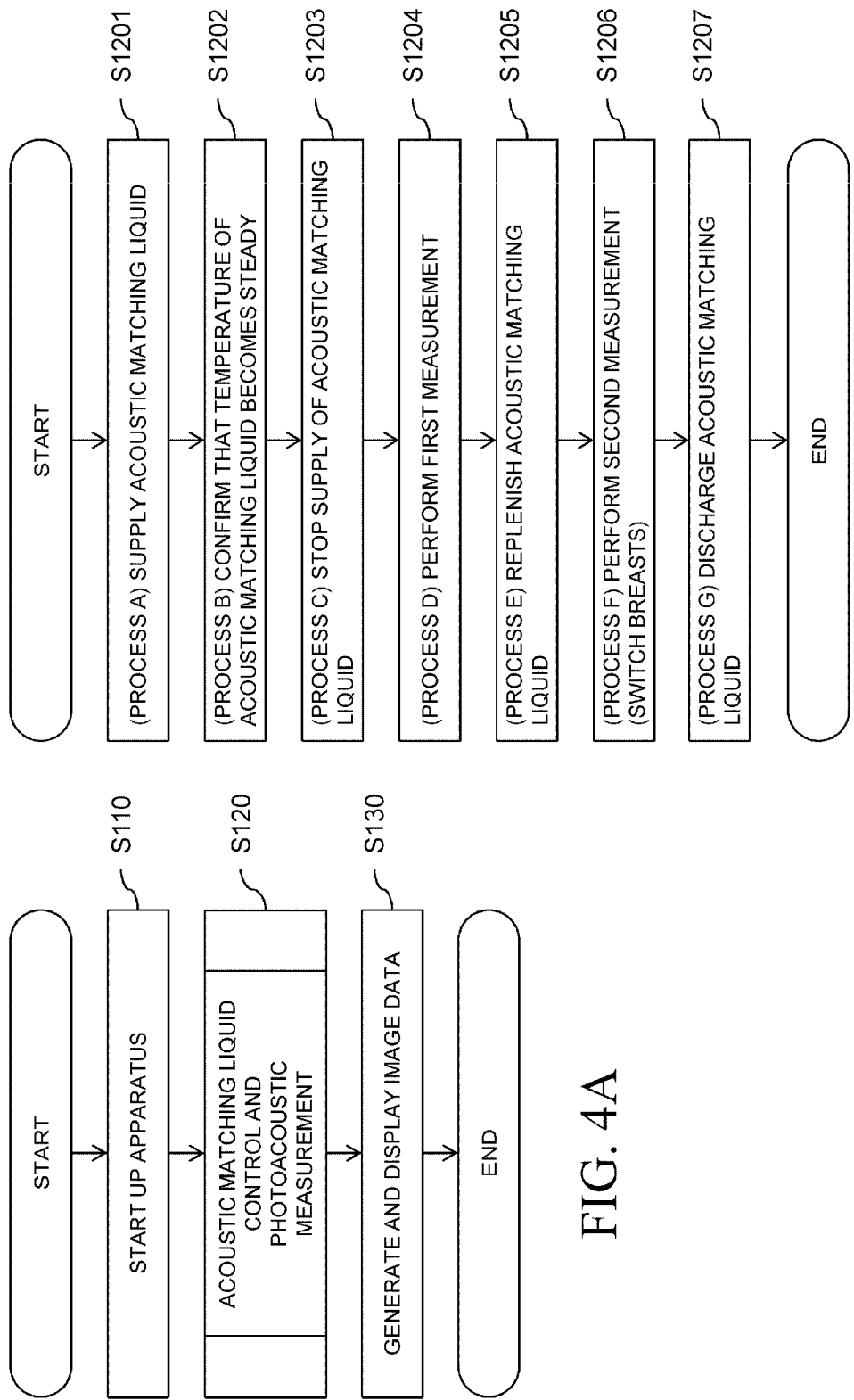
FIGS. 4A and 4B are flow charts showing an acoustic matching liquid supply sequence.

FIG. 4A is a flow chart related to photoacoustic measurement according to the present invention. FIG. 4B is a flow chart showing processes A to G related to acoustic matching liquid control and photoacoustic measurement in an acoustic matching liquid supply sequence. FIGS. 5A to 5D and 6A to 6C respectively correspond to the processes A to G described above and are diagrams illustrating a positional relationship between the liquid vessel 36 and the object holding member 11 and a liquid level of the acoustic matching liquid 35 inside the liquid vessel 36 in each process.

In step S110 in FIG. 4A, a physician or a technician starts up the photoacoustic imaging apparatus and places the apparatus in a measurement-enabled state. At this point, for example, a laser apparatus is warmed up and an information processing apparatus is started up. Once preparations are completed, in step S120, acoustic matching liquid control and photoacoustic measurement are performed and an acoustic signal is acquired. This process will be described later. When measurement is completed, in step S130, the information generating unit 6 generates a photoacoustic image and causes the display unit 7 to display the photoacoustic image.

Hereinafter, steps S1201 (process A) to S1207 (process G) in FIG. 4B will be described by respectively referring to FIGS. 5A to 5D and 6A to 6C.

(Process A)

In step S1201, as shown in FIG. 5A, supply of the acoustic matching liquid 35 is started as preparation for photography by the apparatus. The acoustic matching liquid 35 heated by the liquid supplying system 8 is supplied from a bottom part of the liquid vessel 36. At this point, when a supply port of the acoustic matching liquid 35 is directly underneath the object holding member 11, there is a possibility that bubbles flowing in from the supply port may rise and adhere to the object holding member 11. Bubbles adhered to the object holding member 11 slowly rise along a surface of the object holding member 11. Therefore, once bubbles adhere to the object holding member 11, a long period of time is required for the bubbles to disappear from the surface of the object holding member 11. In consideration thereof, when supplying the acoustic matching liquid 35, the liquid vessel 36 is favorably moved so that the supply port of the acoustic matching liquid 35 is positioned as far away from directly underneath the object holding member 11 as possible.

(Process B)

After the supplied acoustic matching liquid 35 is stored in the liquid vessel 36, in step S1202, the acoustic matching liquid 35 flows out from an upper part of the liquid vessel 36 and returns to the liquid supplying system via the acoustic matching liquid recovery structure 9 as shown in FIG. 5B. Subsequently, the heated acoustic matching liquid 35 is once again supplied from the bottom part of the liquid vessel 36. This circulation is continued until the temperature of the liquid vessel 36 becomes steady. The temperature can be confirmed using the temperature sensors 89a and 89b. For example, it is determined that the temperature has become steady when a temperature variation during a 3-minute period becomes equal to or less than 0.5° C.

(Process C)

Once it is confirmed that the temperature of the acoustic matching liquid 35 has become steady, in step S1203, the examinee inserts a breast to stop the supply of the acoustic matching liquid 35 as shown in FIG. 5C.

(Process D)

In step S1204, as shown in FIG. 5D, when the controlling unit 2 detects that the breast of the examinee has been inserted and the supply of the acoustic matching liquid 35 has been stopped, the controlling unit 2 starts a first measurement. In other words, the supplying rate in step S1204 is going to be 0. When scanning a probe during the measurement, since the liquid vessel 36 containing the acoustic matching liquid 35 is also scanned, the acoustic matching liquid 35 spills from the upper part of the liquid vessel 36 and the amount of the acoustic matching liquid 35 in the liquid vessel 36 gradually decreases.

The object holding member 11 for breasts has a shape in which a central portion protrudes downward. In addition, with the protruding portion as a center, the object holding member 11 is immersed in the liquid vessel storing the acoustic matching liquid to a liquid level which enables propagation of acoustic waves. Therefore, when the amount of the acoustic matching liquid decreases, an outer peripheral part of the object holding member 11 is unable to stay in contact with the acoustic matching liquid. As a result, acoustic waves passing through the outer peripheral part of the object holding member 11 can no longer be acquired.

In consideration thereof, favorably, a measurement of the outer peripheral part of the object holding member 11 is completed before a measurement of an inner peripheral part of the object holding member 11. Accordingly, acoustic waves can be received before the amount of the acoustic matching liquid 35 decreases or, in other words, while the outer peripheral part is still immersed in the liquid. For example, a scanning start position of the receiving unit may be set to an outer peripheral part of a detection region of the object and scanning may be spirally performed so as to draw circles while reducing a radius of rotation. In this manner, by performing scanning so as to move along a spiral trajectory from an outer side toward an inner side, acoustic waves passing through the outer peripheral part of the object holding member 11 can also be acquired.

In addition, it is also favorable to start photoacoustic measurement once a prescribed period of time has elapsed after stopping the supply of the acoustic matching liquid 35 in the present process. Since bubbles adhered to the object holding member 11 may become detached or move upward during the prescribed period of time, a more preferable signal can be acquired. In other words, the supply rate of the acoustic matching liquid 35 in the step 1204 has been reduced to a supplying rate enough not to introduce any bubbles substantially into the liquid vessel 36 with respect to that in the step 1201.

(Process E)

Figure 6A:
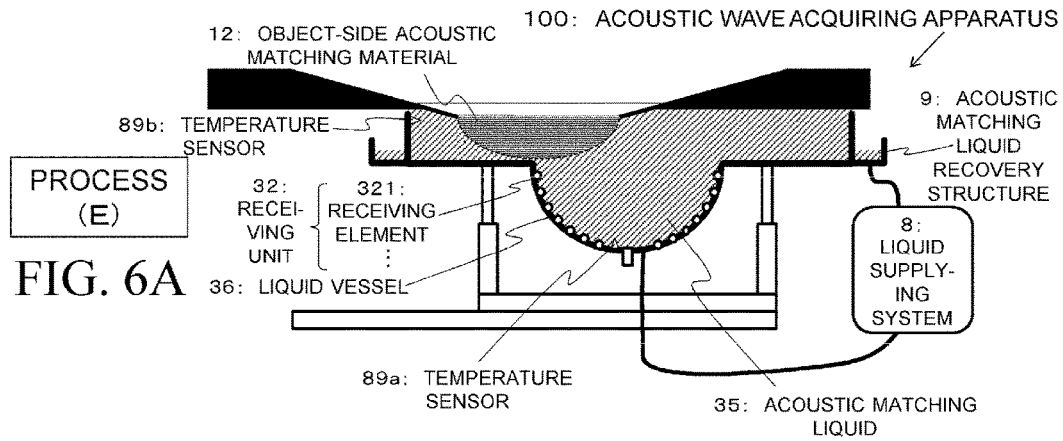
FIGS. 6A to 6C are diagrams showing an acoustic matching liquid supply sequence (from liquid replenishment to end)

Next, the sequence advances to step S1205. When the first measurement is completed, the acoustic matching liquid 35 spills from the upper part of the liquid vessel 36 due to scanning and a state is created where the amount of the acoustic matching liquid 35 in the liquid vessel 36 has decreased. Therefore, in the present process, as shown in FIG. 6A, the examinee separates the breast from the apparatus and the heated acoustic matching liquid is replenished. At this point, the supply port of the acoustic matching liquid 35 once again retreats to a position which avoids being directly underneath the object holding member 11.

(Process F)

Figure 6B:
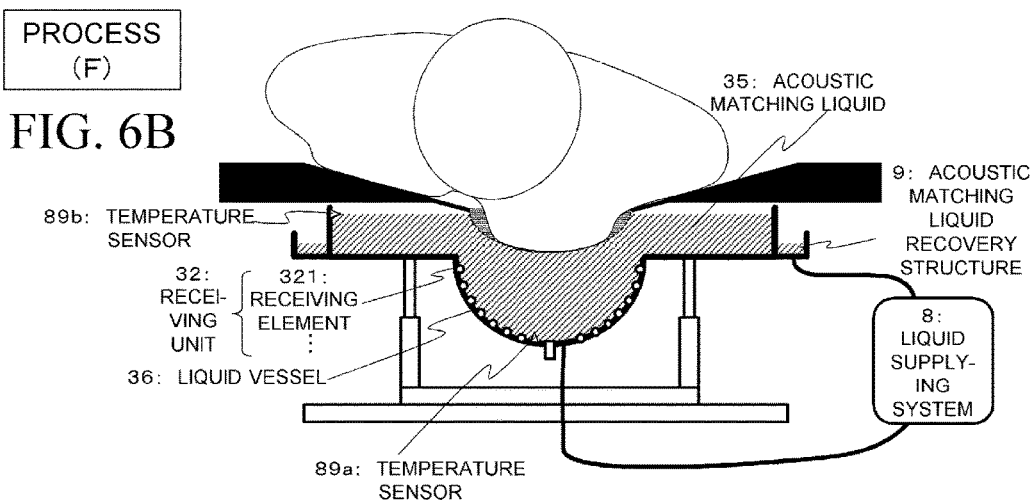

Once it is confirmed that the temperature of the replenished acoustic matching liquid 35 has become steady, in step S1206, the examinee inserts a breast opposite to the breast measured in the first measurement and starts a second measurement as shown in FIG. 6B. At this point, the supply of the acoustic matching liquid 35 is stopped in a similar manner to the first measurement. In addition, the measurement is favorably performed by spirally scanning from an outer peripheral part toward a central part of the object.

(Process G)

Figure 6C:
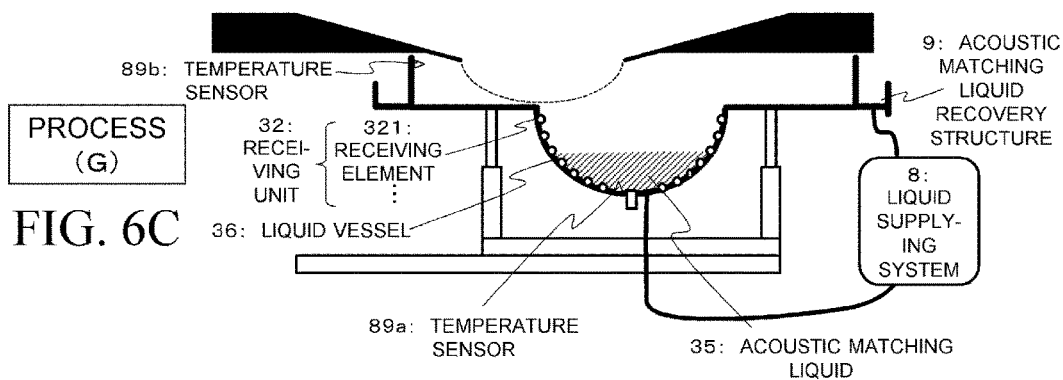

When the second measurement is completed, in step S1207, the acoustic matching liquid 35 stored inside the liquid vessel 36 is discharged from the bottom part of the liquid vessel 36 as shown in FIG. 6C and the series of measurements is completed.

As described above, in the present invention, supplying the acoustic matching liquid 35 heated to around body temperature prevents the examinee from experiencing a cold sensation and reduces a burden on the examinee. In addition, temperature unevenness in the acoustic matching liquid can be reduced by continuously supplying the heated acoustic matching liquid. As a result, since a value of sound velocity on a propagation path of acoustic waves which is necessary when forming an image can be accurately determined, obtained image quality is improved. Furthermore, by stopping the supply of the acoustic matching liquid during photoacoustic measurement, bubbles present between the object and the probe can be reduced. As a result, noise in measured received signals is reduced.

Second Embodiment

In the first embodiment described above, the supply of the acoustic matching liquid 35 is stopped without exception during photoacoustic measurement in order to suppress the creation or adherence of bubbles. In the present embodiment, a photoacoustic imaging apparatus which is an acoustic wave acquiring apparatus 100 includes a bubble detecting unit for confirming an adherence state of bubbles to the object holding member 11. Otherwise, the configuration is similar to that of the first embodiment.

The bubble detecting unit can be configured by, for example, a combination of the light source 5, the camera 33, and the controlling unit 2. In other words, since bubbles have a different reflectance from the surrounding liquid, bubbles exhibit characteristics which differ from their surroundings with respect to light irradiated from the light source 5. In consideration thereof, by performing imaging with the camera 33 in a state where the object holding member 11 is irradiated by light from the light source 5 and analyzing image data obtained by the imaging with the controlling unit 2, a state of presence of bubbles can be confirmed. For example, in the image data, a portion having a bubble shape (for example, a circle or an ellipse with a diameter of 1 mm or less) and having lightness equal to or higher than a prescribed threshold is determined as a bubble. When adopting such a configuration, a bubble detecting unit can be constituted using existing members.

The controlling unit 2 determines whether or not a prescribed amount or more of bubbles are adhered in a region scheduled to be next subjected to photoacoustic measurement in accordance with scanning. An amount of bubbles to be a reference at this point may be determined based on a threshold set in advance or based on desired image quality input by the user using an input unit.

There are various conceivable methods of utilizing information related to a position and an amount of detected bubbles. For example, when it is determined that the position or the amount of bubbles prevents desired accuracy of characteristic information (for example, image quality) from being obtained, photoacoustic measurement can be stopped or information for attracting attention can be presented to the user. In addition, for example, instead of stopping liquid supply without exception in process C, control can be performed so that a supplying rate of the acoustic matching liquid 35 is reduced within a range which does not affect the propagation of acoustic waves and the acoustic matching liquid 35 is continuously supplied during reception of photoacoustic waves. Furthermore, for example, an attempt may be made to remove bubbles using a method such as vibration, stirring, and liquid circulation when bubbles are detected. In addition, for example, when bubbles are detected, a wait time may be set before starting the first measurement in process C. Furthermore, for example, when setting a region of interest in accordance with information input by the user using the input unit, control may be performed in accordance with whether or not bubbles are present in the region of interest.

With the method according to the present embodiment, since appropriate control can be performed in consideration of an actual state of creation or adherence of bubbles, a further improvement in image quality can be achieved. In addition, cost can be contained by having an existing camera or the like double as the bubble detecting unit.

Third Embodiment

In the first embodiment described above, the supply of the acoustic matching liquid 35 is stopped in process C. However, if the creation or adherence of bubbles does not occur or if an amount thereof is negligible from the perspective of image quality, reducing the supplying rate of the acoustic matching liquid 35 during photoacoustic measurement may suffice instead of stopping the supply thereof. A liquid supplying rate in process C in this case differs according to a liquid flow rate, a structure of the pipings, a composition of the acoustic matching liquid, a material of the object holding member 11, and the like. For example, the liquid supplying rate in process C can conceivably be set to 10% or lower than a liquid supplying rate in process A or B.

According to this method, since an outflow of liquid due to scanning of the receiving unit during photoacoustic measurement can be compensated to a certain degree, a probability of the propagation of acoustic waves being inhibited by a shortage of the liquid can be lowered and noise and the like in an acquired image can be reduced.

Fourth Embodiment

In the description given above, a photoacoustic imaging apparatus has been described as an example of the acoustic wave acquiring apparatus 100 according to the present invention. However, the acoustic wave acquiring apparatus 100 according to the present invention may also be an ultrasound echo apparatus. In this case, a difference from the embodiments described above is that an acoustic wave received by a receiving element is not a photoacoustic wave but an echo wave transmitted to and then reflected by an object. The acoustic wave transmitted to the object may be an acoustic wave transmitted by the receiving element itself or may be an acoustic wave transmitted by an element other than the receiving element. Otherwise, an acoustic matching liquid control sequence can be performed in a similar manner to that described above.

Fifth Embodiment

Figure 7A:
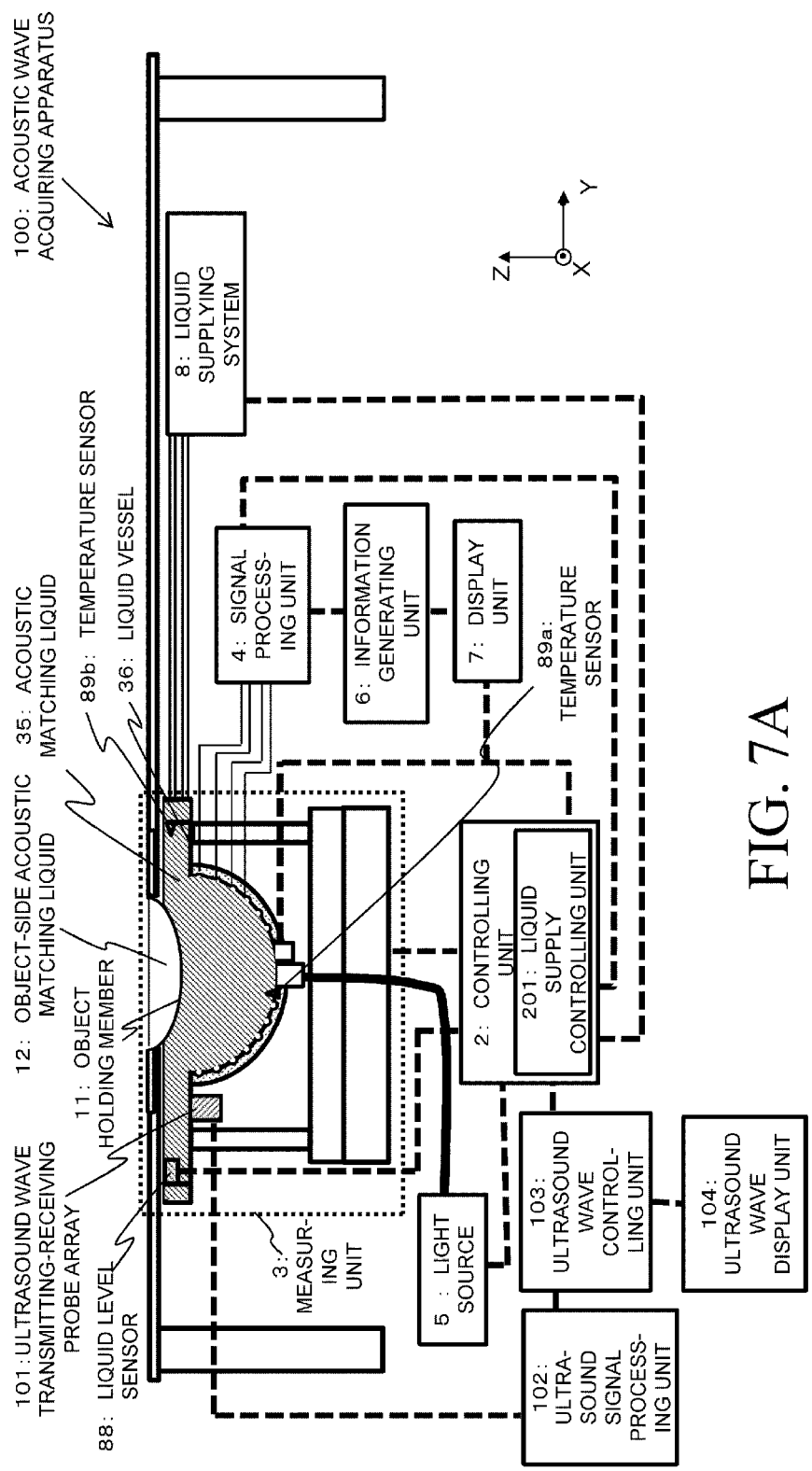
FIG. 7A is a block diagram of an apparatus for both photoacoustic waves and ultrasound echoes.
Figure 7B:
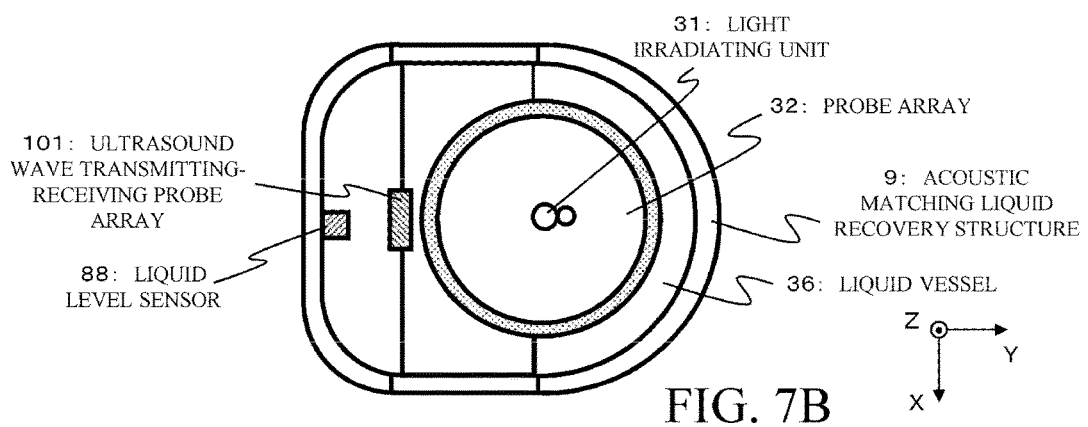
FIG. 7B is another block diagram of an apparatus for both photoacoustic waves and ultrasound echoes.

The present embodiment includes an ultrasound echo measuring function in a similar manner to the fourth embodiment. In the present embodiment, both a photoacoustic measuring mode and an ultrasound echo measuring mode can be executed. FIG. 7 shows the acoustic wave acquiring apparatus 100 according to the present embodiment. FIG. 7A is a schematic sectional view showing an arrangement relationship and a connection relationship of primary components of a photoacoustic measuring apparatus. FIG. 7B is a schematic top view of the liquid vessel 36 shown in FIG. 7A. Moreover, since basic components are similar to those of the respective embodiments described above, the following description will focus on differences from the previous embodiments.

An ultrasound wave transmitting-reception transducer array 101 for ultrasound diagnostics is installed and fixed in a vicinity of a probe array 32 (receiving unit) for photoacoustic measurement on a lower surface of the liquid vessel 36 according to the present embodiment. In the case of this configuration, the scanning unit integrally moves the ultrasound wave transmitting-reception transducer array and the liquid vessel. The ultrasound wave transmitting-reception transducer array 101 including a plurality of ultrasound wave transmitting-receiving elements is favorably set inside the liquid vessel 36 in which the probe array 32 is arranged. Accordingly, since the stored acoustic matching liquid can be shared, the liquid vessel and the liquid supplying system can be downsized. Moreover, the ultrasound wave transmitting-reception transducer array 101 may be arranged at a location closer to the object holding member 11 than the reception transducer array for photoacoustic waves inside the liquid vessel 36. Accordingly, ultrasound signal intensity can be increased, image accuracy can be improved, and the effect of bubbles can be reduced.

The acoustic wave acquiring apparatus 100 according to the present embodiment includes an ultrasound signal processing unit 102, an ultrasound wave controlling unit 103, and an ultrasound wave display unit 104. The ultrasound signal processing unit 102 can be constituted by an information processing apparatus such as a PC or a work station including a processor and a memory in a similar manner to the signal processing unit 4. Moreover, the signal processing unit 4 may double as the ultrasound signal processing unit 102.

The ultrasound wave controlling unit 103 is a circuit which outputs a control signal to a plurality of ultrasound wave transmitting-receiving elements in order to control a transmitted beam or a received beam. Moreover, the controlling unit 2 may issue instructions to the ultrasound wave controlling unit 103 or the controlling unit 2 may double as the ultrasound wave controlling unit 103. The ultrasound wave display unit 104 is a display apparatus capable of displaying information related to ultrasound waves such as image data indicating a characteristic information distribution or control information.

During transmission of an ultrasound wave, the ultrasound wave is transmitted to an object from the ultrasound wave transmitting-reception transducer array 101 via the acoustic matching liquid 35, the object holding member 11, and the acoustic matching material 12. At this point, when a liquid surface height (liquid level) of the acoustic matching liquid 35 is insufficient, a propagation area of the ultrasound wave from the object holding member 11 is restricted and an effective transmission/reception region of an effective acoustic wave is restricted. Therefore, the acoustic matching liquid 35 needs to have a sufficient liquid level at which the effective transmission/reception region of the object supported by the object holding member 11 is sufficiently secured. The effective transmission/reception region can be considered an effective reception region in the photoacoustic measuring mode.

Next, a description will be given on two embodiments of a measurement sequence which is used in an acoustic wave measuring apparatus according to the present embodiment and in which an ultrasound wave transmission/reception measurement and a photoacoustic wave reception measurement are consecutively performed. In a first sequence, the photoacoustic wave reception measurement is performed before the ultrasound wave transmission/reception measurement. In a second sequence, the ultrasound wave transmission/reception measurement is performed before the photoacoustic wave reception measurement. One common feature between the first and second sequences is that a liquid supply sequence of the acoustic matching liquid differs between during the ultrasound wave transmission/reception measurement and the photoacoustic wave reception measurement.

With respect to an ultrasound signal obtained by transmission/reception of ultrasound waves and a photoacoustic signal obtained by reception of photoacoustic waves, a comparison between reflectance of an ultrasound wave and photoacoustic conversion efficiency reveals that the ultrasound signal is greater by one or more orders of magnitude. Therefore, an ultrasound signal is less likely to be affected by a propagation loss due to bubbles in the acoustic matching liquid 35 than a photoacoustic signal. In consideration thereof, in the ultrasound echo measuring mode according to the present embodiment, ultrasound wave transmission/reception is performed without stopping the supply of the acoustic matching liquid unlike in the photoacoustic measuring mode. Accordingly, since new liquid is supplied even when the acoustic matching liquid 35 spills due to scanning or body motion, an acoustic coupling area between the object and the acoustic matching liquid 35 can be maintained during measurement. Measurement with high accuracy can be performed by maintaining the coupling area in this manner.

Figures 8A, 8B:
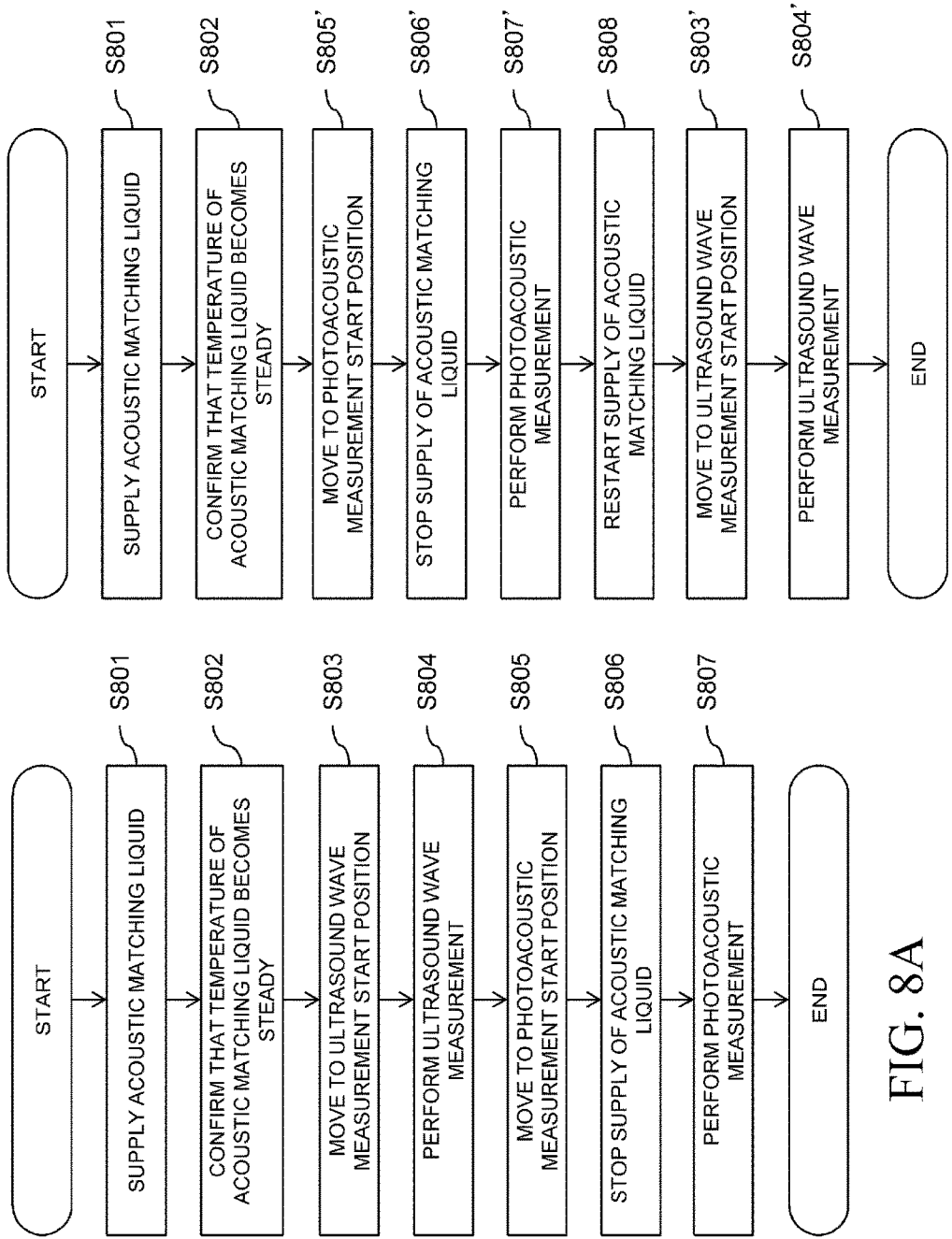
FIGS. 8A and 8B are different flow charts showing an acoustic matching liquid supply sequence.

FIG. 8 is a flow chart showing examples of sequences of acoustic matching liquid supply and stage scanning when performing photoacoustic measurement and ultrasound wave measurement according to the present embodiment. FIG. 8A represents a first sequence in which measurements are performed in an order of the ultrasound wave measurement and the photoacoustic measurement after starting supply of the acoustic matching liquid 35. FIG. 8B represents a second sequence in which measurements are performed in an order of the photoacoustic measurement and the ultrasound wave measurement after starting supply of the acoustic matching liquid 35.

Next, the first sequence will be described in detail. In steps S801 and S802 in FIG. 8A, supply of the acoustic matching liquid 35 to the liquid vessel 36 is started and the temperature sensors 89a and 89b confirm that the temperature of the acoustic matching liquid has become steady.

In step S803, a stage is moved to an ultrasound wave measurement start position while maintaining a supplied state of the acoustic matching liquid 35. In step S804, ultrasound wave measurement is performed by one-dimensionally scanning the ultrasound wave transmitting-reception transducer array. At this point, although scanning of the stage causes the acoustic matching liquid 35 to overflow into an acoustic matching liquid recovery system (groove) provided in an outer periphery of the liquid vessel, since the supply of the acoustic matching liquid 35 is continued, a liquid level sufficient for ultrasound wave measurement is secured. Moreover, the ultrasound wave measurement is performed by scanning the ultrasound wave transmitting-reception transducer array 101, in which transmission/reception probes are one-dimensionally arranged, in a direction intersecting an array direction. The ultrasound wave transmitting-reception transducer array 101 may be scanned in accordance with a boustrophedon scan, a raster scan, or the like.

After the ultrasound wave measurement is finished, in step S805, the receiving unit moves to a photoacoustic measurement start position. In step S806, the supply of the acoustic matching liquid 35 is stopped and, in step S807, photoacoustic measurement is performed.

Next, the second sequence will be described. Steps S801 and S802 in FIG. 8B are similar to FIG. 8A. Subsequently, in step S805', the stage is driven and moved to the photoacoustic measurement start position and the liquid level sensor 88 confirms that a liquid level is at a prescribed position. In step S806', the supply of the acoustic matching liquid 35 is stopped and, in step S807', photoacoustic measurement is performed.

After the photoacoustic measurement, the supply of the acoustic matching liquid 35 is restarted in step S808. In step S803', the stage moves to an ultrasound wave measurement start position. Once the liquid level recovers from a liquid level lowered by a drive operation for photoacoustic measurement to a liquid level sufficient for ultrasound wave measurement, in step S804', ultrasound wave measurement is started.

As described above, by installing the ultrasound wave transmitting-reception transducer array next to the reception transducer array for photoacoustic measurement, photoacoustic measurement information and ultrasound wave diagnostic measurement information can be measured simultaneously and multilateral diagnostics can be realized. In this case, by differentiating supply methods of the acoustic matching liquid for both photoacoustic measurement and ultrasound wave measurement, signal information necessary for optimal image formation with respect to both measurements can be obtained.

Moreover, while one liquid level sensor is used in the present embodiment, in consideration of a fluctuation of the liquid surface or the like which occurs during scanning, liquid level information may be acquired using a plurality of liquid level sensors. In addition, liquid levels in photoacoustic measurement and ultrasound wave measurement may be set to different liquid levels in accordance with respective positions and directionality of the probe array 32 and the ultrasound wave transmitting-reception transducer array 101. Furthermore, in the case of a breast cancer examination or the like, after measuring one breast in accordance with the first or second sequence, the other breast may be examined. In doing so, different sequences may be used for the one breast and the other breast.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-112397, filed on Jun. 6, 2016, which is hereby incorporated by reference herein in its entirety.

What is claimed is:

1. An acoustic wave receiving apparatus comprising:
   a sheet-shaped holding member configured to hold an object on one surface and to cause an acoustic wave propagated from the object to propagate to an opposite surface, the opposite surface being opposite to the one surface;
   a reception transducer array including a plurality of receiving elements configured to receive an acoustic wave propagated from the object via the holding member and to convert the acoustic wave into an electrical signal;
   a liquid vessel to which the reception transducer array is fixed and configured to store an acoustic matching liquid so that the object and the reception transducer array are acoustically coupled to each other;
   a liquid supplying unit configured to supply the acoustic matching liquid to the inside of the liquid vessel;
   a controlling unit configured to control a supplying rate of the acoustic matching liquid to be supplied into the liquid vessel;
   a scanning unit configured to change relative positions of the receiving elements and the liquid vessel with respect to the object; and
   an information generating unit configured to generate characteristic information on the object using the electrical signal,
   wherein the liquid supplying unit is configured to be controlled by the controlling unit so that the supplying rate for a first period of time when the reception transducer array is open to receive the acoustic wave is lower than that for a second period of time when the reception transducer array is not open to receive the acoustic wave.

2. The acoustic wave receiving apparatus according to claim 1, wherein
   the supplying rate for the first period of time is lower than that for the second period of time so as not to introduce bubbles substantially into the liquid vessel.

3. The acoustic wave receiving apparatus according to claim 1, wherein
   the liquid supplying unit is configured to be controlled so that the supplying rate for the first period of time is 0.

4. The acoustic wave receiving apparatus according to claim 1, wherein
   the plurality of receiving elements are configured to receive the acoustic wave after the liquid vessel is filled with the acoustic matching liquid and each of the plurality of receiving elements is acoustically coupled with the object, and
   the controlling unit is configured to set, when the receiving elements receive the acoustic wave, the supplying rate of the acoustic matching liquid from the liquid supplying unit to 10% or lower than when the liquid vessel is filled with the acoustic matching liquid.

5. The acoustic wave receiving apparatus according to claim 1, wherein
the controlling unit is configured to cause the receiving elements to detect the acoustic wave once a prescribed period of time elapses after supply of the acoustic matching liquid from the liquid supplying unit decreases.

6. The acoustic wave receiving apparatus according to claim 1, wherein
the receiving elements are arranged in the liquid vessel and constitute a receiving unit, and
the scanning unit is configured to change relative positions of the receiving unit and the object.

7. The acoustic wave receiving apparatus according to claim 6, wherein
the object has a shape which protrudes from above toward the liquid vessel filled with the acoustic matching liquid, and
the scanning unit is configured to move the receiving unit so that the acoustic wave is first detected in an outer peripheral part of a region of the object immersed in the acoustic matching liquid.

8. The acoustic wave receiving apparatus according to claim 6, wherein
the scanning unit is configured to move the receiving unit so that a region, where an effective reception region in which the receiving unit receives the acoustic wave overlaps with the holding member, moves from an outer side toward an inner side of the holding member.

9. The acoustic wave receiving apparatus according to claim 8, wherein
the scanning unit is configured to move the receiving unit so that the overlapping region traces a spiral trajectory.

10. The acoustic wave receiving apparatus according to claim 1, further comprising:
a light irradiating unit configured to irradiate the object with pulsed light guided from a light source via the holding member, wherein
the receiving elements are configured to receive a photoacoustic wave generated at and propagated from the object when the object is irradiated with the pulsed light.

11. The acoustic wave receiving apparatus according to claim 1, further comprising:
a transmitting-reception transducer array including a plurality of transmitting-receiving elements capable of transmitting and receiving an ultrasound wave to and from the object via the holding member.

12. The acoustic wave receiving apparatus according to claim 11, wherein
the transmitting-reception transducer array is fixed to the liquid vessel.

13. The acoustic wave receiving apparatus according to claim 12, wherein
the transmitting-reception transducer array is fixed to the liquid vessel at a different position from the reception transducer array.

14. The acoustic wave receiving apparatus according to claim 11, wherein
the transmitting-reception transducer array is closer to the holding member than the reception transducer array.

15. The acoustic wave receiving apparatus according to claim 11, wherein
the controlling unit is configured to perform control in:
a photoacoustic measuring mode in which an acoustic wave from the object is received by integrally moving the reception transducer array with the liquid vessel and scanning an effective reception region in which the reception transducer array receives the acoustic wave with respect to the object; and
an ultrasound echo measuring mode in which an ultrasound echo signal from the object is received by integrally moving the transmitting-reception transducer array with the liquid vessel and scanning an effective transmission/reception region with respect to the object, and
a supplying rate of the acoustic matching liquid into the liquid vessel differs between the photoacoustic measuring mode and the ultrasound echo measuring mode.

16. The acoustic wave receiving apparatus according to claim 15, wherein
the photoacoustic measuring mode and the ultrasound echo measuring mode are performed at different timings.

17. The acoustic wave receiving apparatus according to claim 15, wherein
in the photoacoustic measuring mode, a supplying rate of the acoustic matching liquid into the liquid vessel is lower than in the ultrasound echo measuring mode.

18. The acoustic wave receiving apparatus according to claim 17, wherein
the controlling unit is configured to:
stop supply of the acoustic matching liquid into the liquid vessel in the photoacoustic measuring mode; and
continue supply of the acoustic matching liquid into the liquid vessel in the ultrasound echo measuring mode.

19. The acoustic wave receiving apparatus according to claim 15, wherein
the ultrasound echo measuring mode is performed before the photoacoustic measuring mode.

20. The acoustic wave receiving apparatus according to claim 15, wherein
the ultrasound echo measuring mode is performed after the photoacoustic measuring mode.

21. The acoustic wave receiving apparatus according to claim 20, wherein
the controlling unit is configured to supply the acoustic matching liquid to the liquid vessel after the photoacoustic measuring mode and before the ultrasound echo measuring mode.

22. The acoustic wave receiving apparatus according to claim 1, further comprising:
a bubble detecting unit configured to detect bubbles adhered to the holding member, and
the controlling unit is configured to control the liquid supplying unit in accordance with information related to detection of the bubbles.

23. The acoustic wave receiving apparatus according to claim 22, further comprising:
a camera configured to perform imaging of the object, wherein
the camera doubles as the bubble detecting unit.

24. The acoustic wave receiving apparatus according to claim 1, further comprising:
a temperature adjusting apparatus configured to change a temperature of the acoustic matching liquid; and
a temperature sensor configured to detect a temperature of the acoustic matching liquid, wherein
the controlling unit is configured to enable reception of the acoustic wave by the reception transducer array when determination is made that the temperature of the acoustic matching liquid stored inside the liquid vessel has become steady, based on an output of the temperature sensor.

25. A control method of an acoustic wave receiving apparatus including a reception transducer array provided with a plurality of receiving elements, a liquid vessel, and a liquid supplying unit supplying an acoustic matching liquid to the liquid vessel, the control method comprising:

receiving an acoustic wave propagating from an object via a holding member and converting the acoustic wave into an electrical signal;

supplying the acoustic matching liquid into the liquid vessel;

controlling a supplying rate of the acoustic matching liquid to be supplied into the liquid vessel; and generating characteristic information on the object using the electrical signal, wherein the controlling is performed such that the supplying rate for a first period of time when the transducer array is open to receive the acoustic wave is lower than that for second period of time when the transducer array is not open to receive the acoustic wave.

26. The control method of an acoustic wave receiving apparatus according to claim 25, wherein the controlling the supplying rate for the first period of time is controlled so as not to introduce bubbles substantially into the liquid vessel.

27. The control method of an acoustic wave receiving apparatus according to claim 25, wherein the supplying rate for the first period of time is 0.

28. The control method of an acoustic wave receiving apparatus according to claim 25, wherein the receiving of the acoustic wave and the converting of the acoustic wave into an electrical signal is performed by the reception transducer array provided with a plurality of receiving elements.

29. The control method of an acoustic wave receiving apparatus according to claim 25, wherein the supplying of the acoustic matching liquid is performed by the liquid supplying unit.

30. The control method of an acoustic wave receiving apparatus according to claim 25, wherein the controlling of a supplying rate of the acoustic matching liquid is performed by a controlling unit.

31. The control method of an acoustic wave receiving apparatus according to claim 25, the control method further comprises:

changing a relative position of the liquid vessel with respect to the object, wherein the changing of the relative position of the liquid vessel is performed by a scanning unit.

32. The control method of an acoustic wave receiving apparatus according to claim 25, wherein the generating of characteristic information on the object is performed by an information generating unit.

33. The control method of an acoustic wave receiving apparatus according to claim 25, wherein the control method includes:

a photoacoustic measuring mode in which a photoacoustic wave from the object is received; and an ultrasound echo measuring mode in which an ultrasound echo signal from the object is received, wherein a supplying rate of the acoustic matching liquid into the liquid vessel differs between the photoacoustic measuring mode and the ultrasound echo measuring mode.

34. The control method of an acoustic wave receiving apparatus according to claim 33, wherein in the photoacoustic measuring mode, a supplying rate of the acoustic matching liquid into the liquid vessel is lower than in the ultrasound echo measuring mode.

35. The control method of an acoustic wave receiving apparatus according to claim 33, wherein the ultrasound echo measuring mode is performed before the photoacoustic measuring mode.

36. The control method of an acoustic wave receiving apparatus according to claim 33, wherein the ultrasound echo measuring mode is performed after the photoacoustic measuring mode.

37. An acoustic wave receiving apparatus comprising:

a transducer array configured to receive an acoustic wave propagated from an object and to convert the acoustic wave into an electrical signal;

a vessel configured to store an acoustic matching liquid;

a supplying unit configured to supply the acoustic matching liquid in a supplying rate to the inside of the vessel;

a scanning unit configured to change relative position of the transducer array with respect to the object; and an information generating unit configured to generate characteristic information on the object using the electrical signal, wherein the supplying rate in a first period of time when the relative position is to be changed is lower than that in a second period of time when the relative position is not to be changed.

38. The acoustic wave receiving apparatus according to claim 37, wherein the supplying rate in the first period of time is 0.

39. The acoustic wave receiving apparatus according to claim 37, further comprising:

a controlling unit configured to control the supplying rate of the acoustic matching liquid to be supplied into the vessel.

40. The acoustic wave receiving apparatus according to claim 37, wherein the vessel stores the acoustic matching liquid such that the transducer array and the object are acoustically coupled with each other via the stored acoustic matching liquid.

41. The acoustic wave receiving apparatus according to claim 40, further comprising:

a holding member configured to hold the object such that the transducer array and the object are acoustically coupled via the holding member.

42. The acoustic wave receiving apparatus according to claim 37, wherein the transducer array includes a plurality of receiving elements secured to the vessel.

* * * * *